US005500403A

United States Patent [19]
Shafer et al.

[11] Patent Number: 5,500,403
[45] Date of Patent: *Mar. 19, 1996

[54] LIQUID FORMULATIONS AND PROCESS FOR EXTENDING THE VASE LIFE OF CUT FLOWERS

[75] Inventors: Warren E. Shafer, Libertyville; Derek D. Woolard, Waukegan; Neyyan K. P. Samuel, Vernon Hills; Gregory D. Venburg, Deerfield; Bala N. Devisetty, Buffalo Grove; Daniel F. Heiman, Libertyville, all of Ill.

[73] Assignee: Abbott Laboratories, Abbott Park, Ill.

[*] Notice: The portion of the term of this patent shall not extend beyond the expiration date of Pat. No. 5,284,818.

[21] Appl. No.: 259,596

[22] Filed: Jun. 14, 1994

[51] Int. Cl.$^6$ ........................................ A01N 3/02
[52] U.S. Cl. ............................................... 504/115
[58] Field of Search ................................ 504/115, 114

[56] References Cited

U.S. PATENT DOCUMENTS

| | | | |
|---|---|---|---|
| 3,874,871 | 4/1975 | Sy et al. | 504/115 |
| 3,907,539 | 9/1975 | Holdt et al. | 504/115 |
| 5,021,186 | 6/1991 | Ota et al. | 252/186.35 |
| 5,284,818 | 2/1994 | Shafer et al. | 504/115 |

FOREIGN PATENT DOCUMENTS 1240173  8/1988  Canada.

OTHER PUBLICATIONS

DiMartino, "Preservatives CAN make a difference", Florist Magazing, Mar. 1986, pp. 63–65, 73.
Baker et al, Hort Science, 12(1), 38–39, 1977.

Primary Examiner—Allen J. Robinson
Assistant Examiner—Brian Bembenick
Attorney, Agent, or Firm—Jerry F. Janssen

[57] ABSTRACT

Liquid formulations, suitable for use in extending the vase-life of cut flowers and which resist the development of unsightly discoloration and turbidity comprise from about 55 parts by weight to about 98 parts by weight of a sugar; from about 0.05 part by weight to about 1 part by weight of an inhibitor of aminocyclopropanecarboxylate synthase selected from L-trans-2-amino-4-(2-aminoethoxy)-3-butenoic acid and carboxymethoxylamine; from about 0.1 part by weight to about 5 parts by weight of an antimicrobial agent; from about 1 part by weight to about 5 parts by weight of aluminum sulfate; and from about 0.1 part by weight to about 5 parts by weight of a dicarboxylic acid of from two to six carbon atoms. All parts by weight based upon the total weight of the dissolved solid components.

6 Claims, No Drawings

LIQUID FORMULATIONS AND PROCESS FOR EXTENDING THE VASE LIFE OF CUT FLOWERS

TECHNICAL FIELD

This application relates to liquid cut flower preservative formulations and a method for prolonging the vase life of cut ornamental flowers. More particularly the present invention concerns liquid cut flower preservative formulations comprising L-trans-2-amino-4-(2-aminoethoxy)-3-butenoic acid (also known by the common name aminoethoxyvinylglycine and the acronym "AVG") or carboxymethoxylamine (also known by the common name aminooxyacetic acid and the acronym "AOAC"), and a method of prolonging the vase life of cut flowers using such formulations.

BACKGROUND OF THE INVENTION

The marketing of cut flowers and ornamental flowering plants is of considerable economic importance to the horticultural industry. In 1989 the total wholesale United States market for cut flowers and flowering, foliage and bedding plants amounted to approximately 2.43 billion dollars. The sale of cut flowers contributed approximately 459 million dollars to this total, with the sale of potted flowering plants contributing approximately 522 million dollars.

Cut flowers are subjected to considerable stress during harvesting, handling and shipping and their vase life, once in the hands of the consumer, can be shortened considerably due to this stress. Plants produce ethylene, particularly in response to stress, by converting methionine to 1-aminocyclopropane-1-carboxylic acid (known also by the acronym "ACC") and then to ethylene. The enzyme responsible for the conversion of ACC to ethylene is ACC synthase and its activity is known to be inhibited by a number of substances including AVG and AOAA. Ethylene is a gaseous phytohormone produced by plants and flowers and is involved in a number of plant biochemical pathways affecting processes such as abscission, senescence, flowering, fruit setting, fruit ripening, seed germination, sex expression, root growth, internode elongation, epinasty, and geotropism.

A number of formulations are described in the literature and/or are commercially available which aid in extending the vase life of cut flowers. Early formulations employed silver salts, but environmental and toxicity concerns have all but eliminated their use recently. A review of the common ingredients of currently employed formulations for the extension of vase life of cut flowers is provided by A. H. Halevy, et al., *Horticultural Reviews*, 3: 59–143 (1981).

The ingredients of these formulations typically include one or more sugars which provide an energy source for the cut flowers and one or more antimicrobial agents (believed to prevent clogging, by microbial growth, of the vascular system of the cut flower stems). The prior art teaches that the preferred sugar source for cut flowers is glucose or other so-called "reducing" sugars. Most often, these formulations also include citric acid and/or an acidic inorganic salt, such as aluminum sulfate, to lower the pH of the solution into which the cut flowers are placed to a value around pH 3.5–5.0. Aluminum salts are preferred since it is believed that aluminum ion also plays a role in cut flower preservation by affecting the movement of water in the cut flower stems. Representative of cut flower preservative formulations of this type are those disclosed in British patent specification 2,189,676 to Halo Products Close Corporation which include a nonphytotoxic sugar, a pH buffer comprising a mixture of organic acids, and a germicidal agent.

More recently, cut flower preservative formulations have been disclosed in the literature which contain an inhibitor of ACC synthase such as AVG or AOAA. For example, J. E. Baker, et al., *HortScience*, 12(1): 38–39 (1977), have reported that immersing the stems of cut carnations (Dianthus caryophyllus L.) in solutions containing L-trans-2-amino-4-(2-aminoethoxy)-3-butenoic acid ("AVG"), alone or in combination with antimicrobial agents such as sodium benzoate or propyl gallate, extended their vase life. Similar effects on the extension of the vase life of cut flowers following treatment with AVG have been shown for snapdragons (R. E. Hardenburg, et al., *J. Amer. Hort. Soc.*, 102: 517–520); and for irises, daffodils, and chrysanthemums (C. Y. Wang, et al., *Hort. Science*, 14: 59–60). J. S. Lee, et al., *Han'guk Wonye Hakhoechi* (Korean), 31(3): 284–293 (1990, as abstracted in *Chem. Abstr.*, 114(23): 223464c (1991) report that the vase life of Dianthus caryophyllus, variety "White Sim" carnations, was doubled when immersed in distilled water solutions of AOAA. In these instances, the mechanism of action for extension of vase life of the cut flowers has been attributed to the action of AVG in blocking the plant biochemical pathway leading to the production of ethylene.

Typical community well-water supplies are high in hardness and the solutions made up from cut flower preservative formulations containing aluminum salts tend to develop an unsightly turbidity over time due to the formation of aluminum hydroxide flocs or precipitates. Moreover, when these cut flower preservative formulations are acidified by the use of citric acid, microbial growth may occur in the solution with the citric acid serving as a nutrient, leading to unacceptable cloudiness of the solution. If ascorbic acid is employed as the organic acidifying agent, oxidation of the acid causes the development of a yellow color in the solution. In clear cut flower vases, the unsightly cloudiness or yellowing of the water solutions is not acceptable to consumers.

U.S. Pat. No. 5,284,818 discloses stable dry cut flower preservative formulations containing AVG or AOAA, a sugar, aluminum sulfate having from 21 to 27 weight percent water of hydration, and a germicidal agent.

SUMMARY OF THE INVENTION

The present invention provides liquid formulations useful as cut flower preservative solutions which minimize or eliminate the development of turbidity and unsightly coloring. More particularly the present invention provides, in its principle embodiment, cut flower preservative formulations comprising (a) from about 55 parts by weight to about 98 parts by weight of a sugar, (b) from about 0.05 part by weight to about 1 part by weight of an ACC synthase inhibitor selected from L-rans-2-amino-4-(2-aminoethoxy)-3-butenoic acid and carboxymethoxylamine, (c) from about 0.1 part by weight to about 5 parts by weight of an antimicrobial agent, (d) from about 1 part by weight to about 5 parts by weight of aluminum sulfate and (e) from about 0.1 part by weight to about 5 parts by weight of a clarifying agent comprising a dicarboxylic acid of from two to six carbon atoms.

In another embodiment, the formulations of this invention may also further comprise from about 0.1 part by weight to about 5 parts by weight sodium or potassium chloride, from about 0.01 percent by weight to about 2 percent by weight of a nonionic or anionic surfactant.

All parts by weight are based upon total dry weight of the solid components of the formulations.

DETAILED DESCRIPTION

The sugar component of the formulations of the present invention ranges from about 55 to about 97 percent by weight of the total dry formulation, and is selected from the group consisting of sucrose, glucose, and fructose, and mixtures thereof, with glucose being preferred. The ACC synthase activity inhibitor component may be either L-trans-2-amino-4-(2-aminoethoxy)-3-butenoic acid (AVG) or carboxymethoxylamine (AOAA), with AVG being preferred.

The formulations of the present invention also comprise between about 0.1 percent by weight to about 5 percent by weight, preferably about 0.1 percent by weight of an antimicrobial agent. Suitable antimicrobial agents for use in the formulations of this invention include 8-hydroxyquinoline salts (including the citrate or sulfate); chloramphenicol; spectinomycin; alkyl parabens such as methyl, ethyl or propyl paraben and mixtures thereof; salicylic or benzoic acid and their sodium, potassium or ammonium salts; thiabendazole; and alkali metal sorbate salts, especially potassium sorbate; with 8-hydroxyquinoline citrate being preferred.

The formulations of the present invention may also include inorganic salts including from about 0.5 percent by weight to about 5 percent by weight, preferably about 4 percent by weight of an aluminum salt, preferably aluminum sulfate and from about 0.1 percent by weight to about 5 percent by weight, preferably about 0.3 weight percent sodium chloride. An anionic or nonionic surfactant, present in an amount of between about 0.01 percent by weight to about 2 percent by weight, preferably about 0.05 and about 0.5 parts by weight, may also be added to the formulations. Suitable non-ionic surfactant materials useful for the purposes of this invention include, but are not necessarily limited to nonionic surfactants which are partial esters of common fatty acids (e.g. palmitic, stearic and oleic acids) with hexitol anhydrides (hexitans and hexides) derived from sorbitol. These materials are commercially available under the tradename Span® from The Pierce Chemical Co., P.O. Box 117, Rockford, Ill. 61105. Other suitable nonionic surfactants include materials derived from surfactants of the Span® type by etherification of the free hydroxyl groups with poly(oxyethylene) groups. This latter class of surfactants is available under the Tradename Tween® (ICI Americas, Wilmington, Del.). Additionally, polyethoxylated octyl- or nonylphenols (commercially marketed under the tradename Triton®) can also be used. Nonionic surfactants comprising oxyethylated straight chain alcohols, marketed under the tradename Plurafac® by BASF Chemicals, Wyandotte, Mich., as well as nonionic surfactants comprising block copolymers of propylene oxide and ethylene oxide, marketed under the tradename Pluronic® (BASF) can also be used. Additionally, nonionic surfactants which are block polymers of polyoxyalkylene derivatives of ethylenediamine, marketed under the tradename Tetronic® surfactants (BASF) may be used. Preferred nonionic surfactants in the formulations of the present invention are surfactants of the Pluronic® type, particularly Pluronic® F-68. Suitable anionic surfactants include alkali metals salts of esters of sulfosuccinic acid such as sodium dioctyl sulfosuccinate, marketed under the tradename Areosol OT® (American Cyanamid, Wayne, N.J.

The organic acid employed as the acidifying/clarifying agent of the present invention is selected from the group consisting of dicarboxylic acids of two six carbon atoms, for example oxalic acid, maleic acid, malonic acid, malic acid, tartaric acid, citraconic acid, itaconic acid, diglycolic acid, and the like, with tartaric acid being preferred. As shown by the Examples presented below, all three of these acids have the ability to maintain the pH of the cut flower preservative solutions in the desired range of under pH 4 during the duration of use. However, unlike citric acid which is taught in the prior art for this purpose, these acids also prevent both the discoloration of the aqueous cut flower solutions as well as their development of unsightly turbidity.

In general, the formulations of the present invention are prepared as aqueous solutions, preferably as concentrates for later dilution prior to use, or as solutions at the concentration intended for end use. The formulations are prepared generally by first screening the materials through a 10 mesh screen and then blending, under dry conditions, the screened components. The dry mixture is then dissolved in water to make up the aqueous solutions. Alternatively, the solutions are prepared by mixing one or more of the solid ingredients into water in a serial manner. The solutions are made up in the concentrations which are ultimately used as cut flower preservative solutions or, preferably in concentrations which are diluted later just prior to use. When formulated as concentrates, the solutions are prepared at concentrations ranging between about ten and about seventy-five times that typically employed by the end-user. The upper concentration limit is determined by the solubility limit of the least soluble solid component of the formulations. Preferable concentrations range between about twenty and seventy times the final end-use concentration. The solutions may also optionally contain a coloring agent such as FD&C Blue No. 1. If employed, the dye is prepared by adding 0.25 parts by weight of the dye to 99.75 parts by weight water prior to dissolving the other solid components of the cut flower preservative.

To enhance the life of the aqueous cut flower solutions or concentrates, the liquid solutions are filled into air-tight containers and may be de-gassed with nitrogen to remove air or oxygen. It is preferred that the liquid solutions be refrigerated prior to use to also extend their life prior to use.

EXAMPLE 1

A typical batch of liquid concentrate cut flower preservative formulation in accordance with the present invention was prepared by thorough dry blending of the following components in the amounts indicated and then dissolving the resulting dry mixture in water to make up the final aqueous solution.

TABLE 1

| Component | Amount | Percent by Weight |
|---|---|---|
| AVG | 1.570 g | 0.35 |
| Potassium sorbate | 0.043 g | 0.27 |
| Sodium benzoate | 0.043 g | Combined |
| 8-Hydroxyquinoline citrate | 1.090 g | Preservatives |
| Sodium chloride | 0.650 g | 0.15 |
| Poloxamer 188 Surfactant | 0.430 g | 0.10 |
| Aluminum sulfate | 8.36 g | 1.91 |
| Tartaric acid | 1.30 g | 0.30 |
| Sucrose | 424.5 g | 96.92 |

The mixture of solids listed above was dissolved in 561.89 g of water to prepare the liquid concentrate solution.

EXAMPLES 2–9

In the following Examples, a series of experiments were conducted in which various organic acids were evaluated in place of the tartaric acid listed above as potential clarifying/acidifying agents in cut flower preservative formulations of this invention. In each instance, the cut flower preservative formulation had the composition given above in Example 1, but the identify of the organic acid varied from one Example to the next.

In Examples 2–9 the dry ingredients were weighed and mixed, and the mixed solids dissolved in tap water to simulate end-use condition. Each solution was stirred for ten minutes and an initial turbidity measurement taken. These initial turbidity readings were considered "time zero" turbidity readings. In each case the solution was dispensed in 500 mL batches into one-quart vases, with seven duplicate vases for each organic acid tested.

Floral bouquets of miniature carnations, alstroemeria, bouvardia, delphiniums, cushion mums, daisy mums, and salal were prepared by cutting the stems of each flower to a length of about twelve inches under the surface of deionized water. The flowers, thus prepared, were distributed to the various vases so that a similar bouquet was placed in each vase.

The vases were arranged under fluorescent lighting and allowed to stand at room temperature for the duration of the experiment. After twenty-four hours, 2.5 mL samples were removed from each of the seven duplicate vases for each test organic acid and the samples thus collected were pooled and measured for pH and turbidity. All turbidity measurements were made using a previously calibrated Hach Turbidimeter (Hach Co., Loveland, Colo.) Calibration was achieved by using gelex turbidity standards of 2, 20, and 200 normal turbidity units (NTU'). Measurement of the turbidity of deionized water by this method generally gave values of about 2 NTU. For purposes of evaluation, turbidity readings below 10 NTU did not have visually perceivable turbidity, and were chosen to represent turbidities of visually clear solutions.

The results of these measurements are presented in Table 2 below.

All of the acids employed in the experiments maintained the pH of the solution in the range of about pH 4.0 to pH 4.5 over the duration of the experiments, with citric acid maintaining the pH of the solution in the range of pH 3.7 to pH 3.9 over the same period. In this regard, there was little difference between the various organic acids tested.

However, examination of the data in Table 2 shows that there was considerable variation in the ability of the various acids tested to maintain the clarity of the cut flower preservative solutions over a ten-day period. While all of the acids, with the exception of ascorbic, had an initial turbidity reading in the range of 2.0–2.6 (visually very clear), by the end of the ten-day period of the experiment, the solutions ranged from that of the preferred still visually clear tartaric acid (9.3 NTU) to the unacceptably very cloudy fumaric acid (29.0 NTU). If a slightly higher turbidity value of about 13 to about 15 NTU is accepted as showing only slightly perceivable visual cloudiness of the aqueous cut flower preservative solutions, then malonic, maleic, malic and salicylic acid are also acceptable acidifying/clarifying agents for use in the cut flower preservative formulations of the present invention.

Thus, while the prior art teaches that an acid, particularly citric acid, should be added to cut flower preservative solutions to maintain the pH of the solution at a value of about pH 3.0–pH 4.0, these experiments illustrate that the choice of acid is critical if it is desired to maintain the clarity of the aqueous solution in the vase over the duration of the life of the cut flower bouquet, as extended by the action of the cut flower preservative.

While there have been shown and described what are believed to be the preferred embodiments of the present invention, it will be obvious to one of ordinary skill in the art that various modifications can be made in the Examples without departing from the scope of the present invention as it is defined by the appended claims.

We claim:

1. An aqueous cut flower preservative formulation comprising (a) from about 55 parts by weight to about 98 parts by weight of a sugar,

TABLE 2

Effect of Various Organic Acids on the Clarity of Aqueous Solutions of Cut Flower Preservatives Over a Ten-Day Period

| Example Acid | Normal Turbidity Units (NTU's) | | | | | | | | | |
| --- | --- | --- | --- | --- | --- | --- | --- | --- | --- | --- |
| | Day 1 | Day 2 | Day 3 | Day 4 | Day 5 | Day 6 | Day 7 | Day 8 | Day 9 | Day 10 |
| Example 2 Tartaric | 2.6 | 3.5 | 2.4 | 3.1 | 3.5 | 7.5 | 6.8 | 8.1 | 8.5 | 9.3 |
| Example 3 Malic | 2.4 | 3.9 | 2.5 | 2.2 | 7.1 | 13.0 | 10.0 | 11.0 | 11.9 | 13.4 |
| Example 4 Malonic | 2.4 | 3.4 | 2.4 | 2.9 | 8.2 | 12.4 | 11.3 | 11.5 | 13.6 | 14.1 |
| Example 5 Maleic | 2.3 | 2.3 | 2.5 | 2.6 | 3.5 | 5.3 | 6.1 | 7.5 | 7.8 | 15.0 |
| Example 6 Fumaric | 2.3 | 2.3 | 2.5 | 2.5 | 9.0 | 17.9 | 14.1 | 16.0 | 19.5 | 29.0 |
| Example 7 Salicylic | 2.3 | 2.7 | 2.0 | 2.7 | 5.8 | 8.9 | 8.2 | 10.5 | 11.9 | 14.3 |
| Example 8 Ascorbic | 5.9 | 12.8 | 11.2 | 7.6 | 13.1 | 16.5 | 15.0 | 13.9 | 16.9 | 18.2 |
| Example 9 Citric | 2.0 | 2.4 | 2.7 | 3.1 | 10.4 | 15.2 | 12.3 | 14.3 | 16.0 | 18.2 |

(b) from about 0.05 part by weight to about 1 part by weight of an ACC synthase inhibitor selected from L-trans-2-amino-4-(2-aminoethoxy)-3-butenoic acid and carboxymethoxylamine, (c) from about 0.1 part by weight to about 5 parts by weight of an antimicrobial agent, (d) from about 1 part by weight to about 5 parts by weight of aluminum sulfate, and (e) from about 0.1 part by weight to about 5 parts by weight of an acidifying/clarifying agent selected from the group consisting of maleic acid, malonic acid, malic acid, salicyclic acid, and tartaric acid.

2. A liquid cut flower preservative formulation as defined by claim 1 wherein said acidifying/clarifying agent is tartaric acid.

3. A liquid cut flower preservative formulation as defined by claim 1 further comprising from about 0.01 percent by weight to about 2 percent by weight of a nonionic or anionic surfactant.

4. A liquid cut flower preservative formulation as defined by claim 2 wherein said acidifying/clarifying agent is present in an amount of between about 0.1 parts by weight and 3 parts by weight based upon the total weight of all solid components of the formulation.

5. An aqueous liquid cut flower preservative formulation which resists the development of discoloration and turbidity over the duration of its use comprising (a) from about 55 parts by weight to about 98 parts by weight of a sugar, (b) from about 0.05 part by weight to about 1 part by weight of an ACC synthase inhibitor selected from L-trans-2-amino-4-(2-aminoethoxy)-3-butenoic acid and carboxymethoxylamine, (c) from about 0.1 part by weight to about 5 parts by weight of an antimicrobial agent, (d) from about 1 part by weight to about 5 parts by weight of aluminum sulfate;

(e) from about 0.1 part by weight to about 5 parts by weight of tartaric acid;

(f) from about 0.1 to about 5 parts by weight sodium or potassium chloride; and (g) from about 0.01 to about 0.5 parts by weight of a nonionic or anionic surfactant;

all parts by weight based upon the total weight of all solid components.

6. An aqueous cut flower preservative formulation as defined by claim 1 wherein said ACC synthase inhibitor is L-trans-2-amino-4-(2-aminoethoxy)-3-butenoic acid.

* * * * *

UNITED STATES PATENT AND TRADEMARK OFFICE
CERTIFICATE OF CORRECTION

PATENT NO. : 5,500,403

DATED : March 19, 1996

INVENTOR(S) : Warren E. Shafer, Derek D. Woolard, Neyyan K. P. Samuel, Gregory D. Venburg, Bala N. Devisetty, and Daniel F. Heiman It is certified that error appears in the above-indentified patent and that said Letters Patent is hereby corrected as shown below:

In column 3, line 16 delete "0.1" and insert --0.5--..

In column 3, line 65 delete "N.J." and insert --N.J.).--.

In column 5, line 9 delete "condition" and insert --conditions--.

In column 5, line 32 delete "(NTU')" and insert --(NTU'S)--.

Signed and Sealed this

Twenty-fourth Day of December, 1996

Attest:

BRUCE LEHMAN

Attesting Officer    Commissioner of Patents and Trademarks